(12) United States Patent
Ellis et al.

(10) Patent No.: US 11,197,942 B2
(45) Date of Patent: Dec. 14, 2021

(54) SYSTEMS AND METHODS FOR PURIFYING AN ENVIRONMENT

(71) Applicant: RGF ENVIRONMENTAL GROUP, INC., Riviera Beach, FL (US)

(72) Inventors: Walter B. Ellis, Jupiter, FL (US); Ronald G. Fink, Jupiter, FL (US)

(73) Assignee: RGF ENVIRONMENTAL GROUP, INC., Riviera Beach, FL (US)

( * ) Notice: Subject to any disclaimer, the term of this patent is extended or adjusted under 35 U.S.C. 154(b) by 204 days.

(21) Appl. No.: 16/172,186

(22) Filed: Oct. 26, 2018

(65) Prior Publication Data

US 2019/0125919 A1     May 2, 2019

Related U.S. Application Data

(60) Provisional application No. 62/578,136, filed on Oct. 27, 2017.

(51) Int. Cl.
    *A61L 9/22*          (2006.01)

(52) U.S. Cl.
    CPC ...................... *A61L 9/22* (2013.01)

(58) Field of Classification Search
    CPC ........................................................ A61L 9/22
    See application file for complete search history.

(56) References Cited

U.S. PATENT DOCUMENTS

| | | | |
|---|---|---|---|
| 2005/0210902 A1* | 9/2005 | Parker | F24F 3/166 62/230 |
| 2015/0248989 A1* | 9/2015 | Ezaki | A61L 9/22 313/230 |
| 2018/0243462 A1* | 8/2018 | Okano | A61L 9/22 |

OTHER PUBLICATIONS

Pretlove, Basic Vibration Theory and its Application to Beams and Plates (Year: 1995).*
PI USA, ULtrasonic Piezo transducers (Year: 2020).*

* cited by examiner

*Primary Examiner* — Kevin Joyner
*Assistant Examiner* — Brendan A Hensel
(74) *Attorney, Agent, or Firm* — Rothwell, Figg, Ernst & Manbeck, P.C.

(57) ABSTRACT

In some embodiments, a system for purifying an environment may be provided. The system may include a first electrode which may be exposed to air. The system may include a first transducer which may be configured to apply a first energy to the first electrode and a second transducer which may be configured to apply a second energy to the first electrode. The system may be configured such that at a first time, the first transducer applies the first energy to the first electrode and the second transducer does not apply the second energy to the first electrode. The system may be further configured such that at a second time, the second transducer applies the second energy to the first electrode.

18 Claims, 10 Drawing Sheets

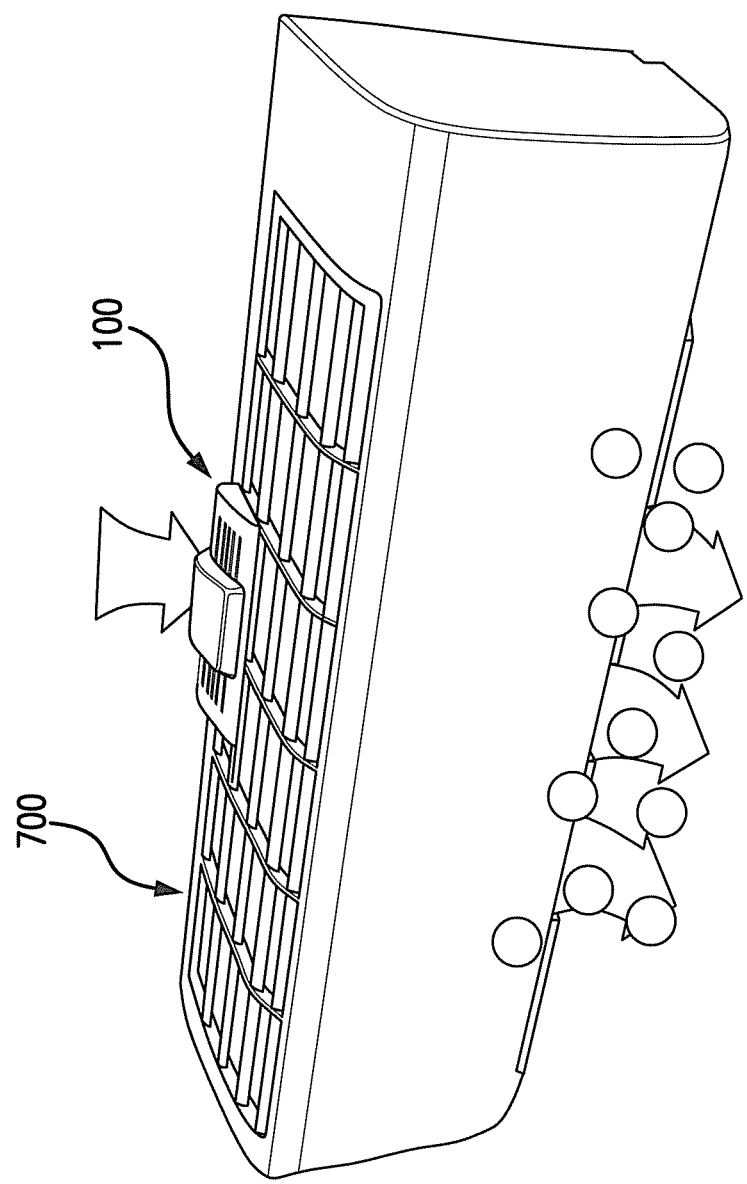

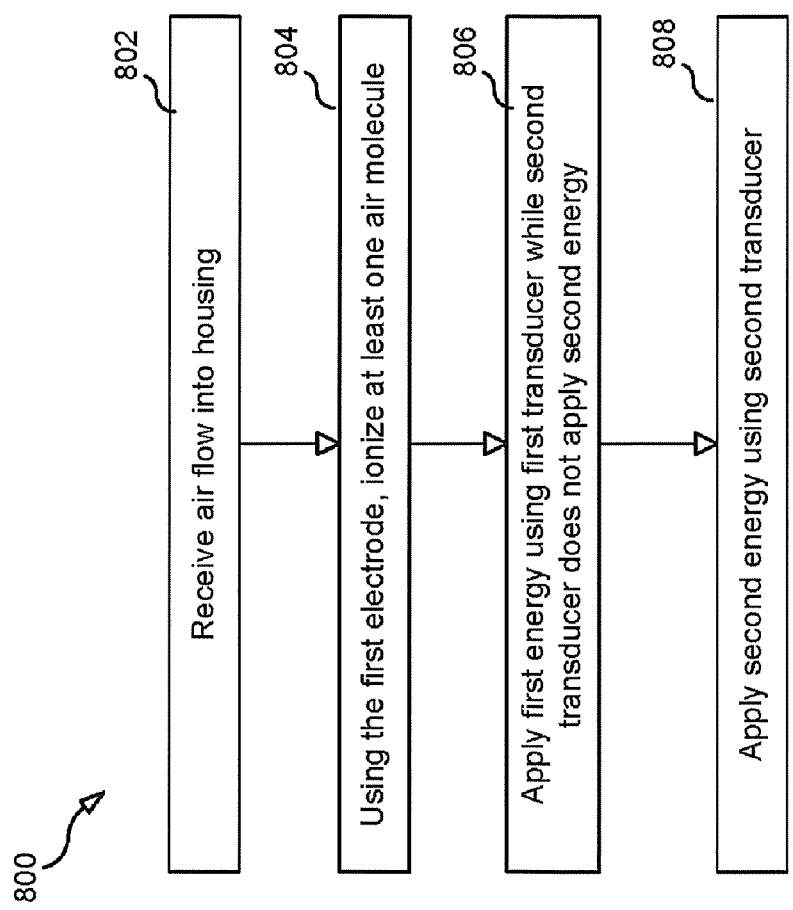

SYSTEMS AND METHODS FOR PURIFYING AN ENVIRONMENT

PRIORITY CLAIM AND CROSS-REFERENCE TO RELATED APPLICATIONS

The present application claims priority to U.S. Provisional Patent Application Ser. No. 62/578,136, filed Oct. 27, 2017, which is hereby incorporated by reference in its entirety.

FIELD OF THE DISCLOSURE

This disclosure generally relates to systems and methods for purifying environments, such as indoor or outdoor spaces. More specifically, this disclosure relates to ion generating purification systems and methods incorporating a self-cleaning capacity.

BACKGROUND

Ion generator technology can be an effective way to reduce particulate, microbial, and volatile organic compound (VOC) contaminants. Ion generators may operate by applying a voltage to an electrically conductive electrode. The charged electrode may be exposed to air and may ionize passing air molecules.

Due to their charged nature, particles in the air may be attracted to the electrodes. Over time, particles may build up and cover the electrodes, which can reduce the efficiency of the system. Accordingly, there is a need for systems that can reduce the build-up of such particles.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

In some embodiments, a system for purifying an environment may be provided. The system may include a first electrode which may be exposed to air. The system may further include a first transducer which may be configured to apply a first energy to the first electrode. The system may include a second transducer which may be configured to apply a second energy to the first electrode. The system may include a controller which may be configured to control one or both of the first transducer and the second transducer. The system may be configured such that at a first time, the first transducer applies the first energy to the first electrode and the second transducer does not apply the second energy to the first electrode. The system may be further configured such that at a second time, the second transducer applies the second energy to the first electrode.

In some embodiments, the first electrode may be a brush comprising a plurality of bristles. In some embodiments, applying the first energy to the first electrode may cause one or more bristles of the plurality of bristles to oscillate. In some embodiments, applying the second energy to the first electrode may cause the one or more bristles of the plurality of bristles to oscillate at a greater magnitude than does applying the first energy to the plurality of bristles. In some embodiments, the brush may have a length and a transverse dimension perpendicular to its length. In some embodiments, the length may be at least 4 times the transverse dimension. In some embodiments, the length may be at least 6 times the transverse dimension. In some embodiments, the length may be at least 8 times the transverse dimension.

In some embodiments, the first transducer may be an ultrasonic transducer. In some embodiments, the second transducer may be a vibration motor.

In some embodiments, the first energy may be applied to the first electrode substantially continuously when the controller is in a powered-on state. In some embodiments, the second transducer may be operably connected to a timing circuit such that the second energy is applied to the first electrode at intervals.

In some embodiments, the system may include a second electrode and a third transducer. In some embodiments, the third transducer may be configured to apply a third energy to the second electrode. In some embodiments, the second transducer maybe configured to apply the second energy to both the first electrode and the second electrode.

In some embodiments, the system may include a housing which may enclose one or more of the first electrode, the second electrode, the first transducer, the second transducer, and/or the third transducer (where such elements are included in a given embodiment).

In some embodiments, the first electrode may have a negative polarity and the second electrode may have a positive polarity. In some embodiments, the polarity of each electrode may alternate such that at any given time, the polarities of the electrodes are opposite but neither the first electrode nor the second electrode has a fixed polarity. In some embodiments, the first electrode may be separated from the second electrode by a distance that is at least one third of a length of the housing. In some embodiments, the distance may be at least one half the length of the housing. In some embodiments, the distance may be at least three quarters the length of the housing.

In some embodiments, a system for purifying an environment may include a first electrode which may be exposed to air. The system may include a first transducer configured to apply a first energy to the first electrode. The system may include a controller which may be configured to control the first transducer. In some embodiments, the system may be configured such that at a first time, the first transducer applies the first energy to the first electrode. In some embodiments, the system may be configured such that at a second time, the first transducer does not apply the first energy to the first electrode.

In some embodiments, the system may further include a second transducer which may be configured to apply a second energy to the first electrode. In some embodiments, the second transducer may be an ultrasonic transducer. In some embodiments, applying the second energy to the first electrode may cause one or more bristles of the plurality of bristles to oscillate at a lesser magnitude than does applying the first energy to the plurality of bristles. In some embodiments, the second energy may be applied to the first electrode substantially continuously when the controller is in a powered-on state.

In some embodiments, the first transducer maybe operably connected to a timing circuit such that the second energy is applied to the first electrode at intervals.

In some embodiments, the system may include a second electrode. In some embodiments, the first transducer may be configured to apply the first energy to both the first electrode and the second electrode.

In some embodiments, the system may include a mechanical coupling which may be configured to conduct vibration energy. In some embodiments, the mechanical coupling may be coupled to each of the first transducer, the first electrode, and the second electrode. In some embodiments, a transducer may be substantially equidistant between the first electrode and the second electrode.

In some embodiments, a method for purifying an environment may be provided. In some embodiments, the method may be performed in a system including a housing, a first electrode, a first transducer configured to apply a first energy, a second transducer configured to apply a second energy, and/or a controller. In some embodiments, the method may include receiving a flow of air into the housing. In some embodiments, the method may include using the first electrode to ionize at least one air molecule of the air flow. In some embodiments, the method may include applying the first energy to the first electrode but not applying the second energy to the first electrode at a first time. In some embodiments, the method may include applying the second energy to the first electrode at a second time.

In some embodiments, applying the first energy and/or the second energy to the first electrode may be effective to remove particulate build-up from the first electrode.

In some embodiments, the first electrode may be a brush including a plurality of bristles. In some embodiments, applying the first energy to the first electrode may cause one or more bristles of the plurality of bristles to oscillate. In some embodiments, applying the second energy to the first electrode may cause the one or more bristles of the plurality of bristles to oscillate at a greater magnitude than does applying the first energy to the plurality of bristles.

In some embodiments, the method may include determining, using a timing circuit, that an interval of time has elapsed since the second energy was last applied to the first electrode. In some embodiments, the method may include applying the second energy to the first electrode in response to determining that the interval of time has elapsed.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 5-7 depict an HVAC system with a purification system according to some embodiments installed on or in the HVAC system.

FIG. 8 depicts a method for purifying according to some embodiments.

DETAILED DESCRIPTION

Figure 1A:
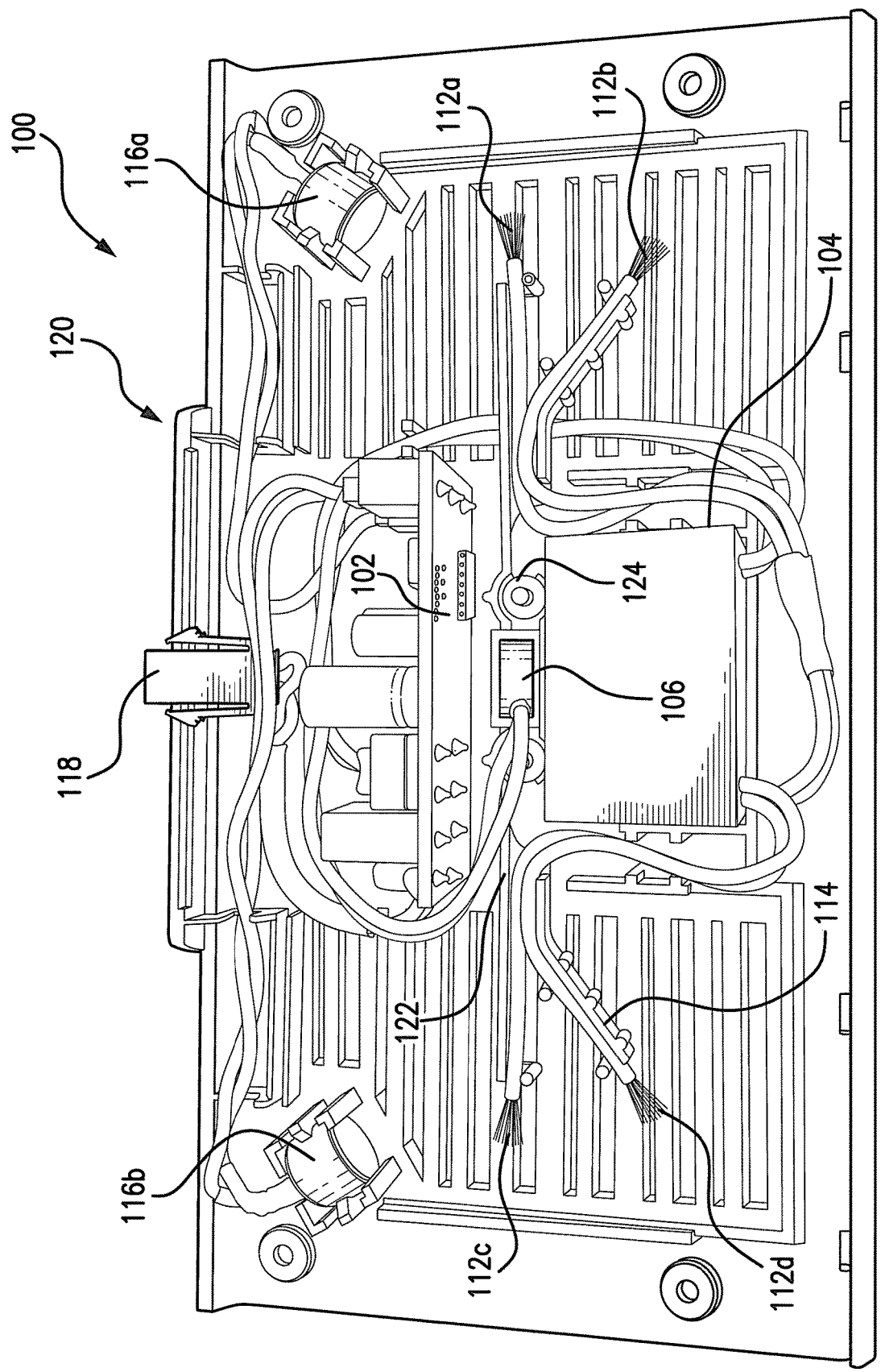
FIGS. 1A and 1B illustrate systems for purifying environments according to some embodiments.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

The purification systems disclosed herein may be used to purify any suitable environment. For example, the systems and methods may be used to purify indoor or outdoor spaces, and they may be further used to eliminate contaminants in any suitable medium, including air and fluids. In some embodiments, these systems may be operably connected to an HVAC system to purify air in an indoor environment. In some embodiments, these systems may be arranged within a duct of an HVAC system or coupled to an intake of a ductless HVAC system such as a mini-split.

FIG. 1A illustrates an exemplary system 100 for purifying an environment. In some embodiments, the system may include a housing 120 having a length L. In some embodiments, the housing 120 may house one, some, or all of the electronic components of the system described herein. In some embodiments, a power input 118 may extend through a wall of the housing 120 to permit an external power supply to be coupled to electrical components within the housing 120.

In some embodiments, the system 100 may include a controller 102, an ion generator 104, and one or more electrodes 112a-112d. Although four electrodes are depicted in the illustrated embodiment, any suitable number of electrodes may be used. In some embodiments, one, two, three, four, five, six, seven, eight or more electrodes may be used. One or more of the electrodes 112a-112d may be exposed to air molecules passing through the system 100. The electrodes 112a-112d may be electrically coupled to the ion generator 104. In some embodiments, the ion generator 104 may transmit via conductive wires a voltage to the electrodes 112a-112d. In some embodiments, the electrodes may carry a voltage from 3,000 volts to 10,000 volts or more. In some embodiments, the charge may be approximately 4,000, 5,000, 6,000, 7,000, 8,000, or 9,000 volts. In some embodiments, the electrodes may transmit a current of less than 30 microamps. In some embodiments, the current may be between approximately 8 and 15 microamps.

In some embodiments, the system 100 may include two or more different types of transducers that apply two or more different types of energy. For example, transducer 106 may apply a first type of energy to one or more of the electrodes 112a-112d, and transducers 116a, 116b may apply a second type of energy to one or more of the electrodes 112a-112b. In some embodiments, transducer 106 may be a vibration motor that transmits mechanical oscillatory energy to the electrodes 112a-112d. In some embodiments, transducers 116a, 116b may be ultrasound transducers that transmit ultrasound energy to the electrodes 112a-112d. In addition to reducing the build-up of particles on electrodes, the use of ultrasound transducers may additionally act as a pest deterrent to species that are caused discomfort by energy at an ultrasonic frequency. Although a single vibration motor and two ultrasound transducers are depicted in the illustrated embodiment, any suitable number of transducers (whether of a first transducer type, a second transducer type, or otherwise) may be used.

For some transducers such as ultrasound transducers, it may be advantageous to arrange electrodes in a line so that a single transducer may apply energy to more than one electrode. For example, electrodes 112a, 112b may be arranged on a line, and transducer 116a may be oriented to apply energy along that line. Likewise, electrodes 112c, 112d may be arranged on a line, and transducer 116b may be oriented to apply energy along that line. In some embodiments, the transducers 116a, 116b may be arranged such that the transducers 116a, 116b are disposed on the respective lines and oriented such that the energy output is directed along these lines.

In some embodiments, the system 100 may include a mechanical coupling that may be coupled to one, some, or all of the electrodes 112a-112d and the transducer 106 (or transducers 106 in embodiments with multiple such transducers). In some embodiments, the mechanical coupling may include a base 122 or a frame 222 on which elements such as transducer 106 and electrodes 112a-112d may be mounted. In some embodiments, the ion generator 104 and/or controller 102 may also be mounted on the base 122 or frame 222.

Figure 2A:
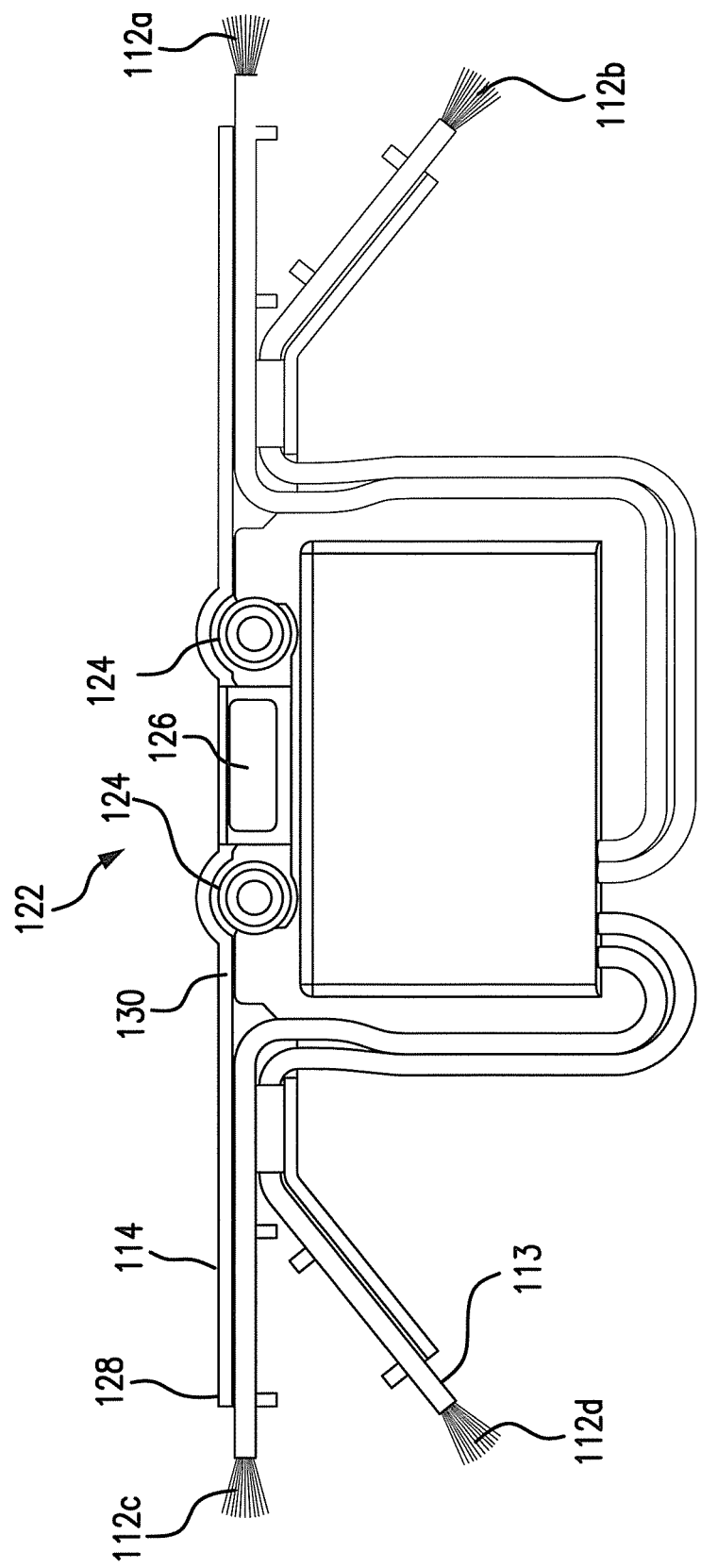
FIGS. 2A and 2B depict frames for purification systems according to some embodiments.
Figure 2B:
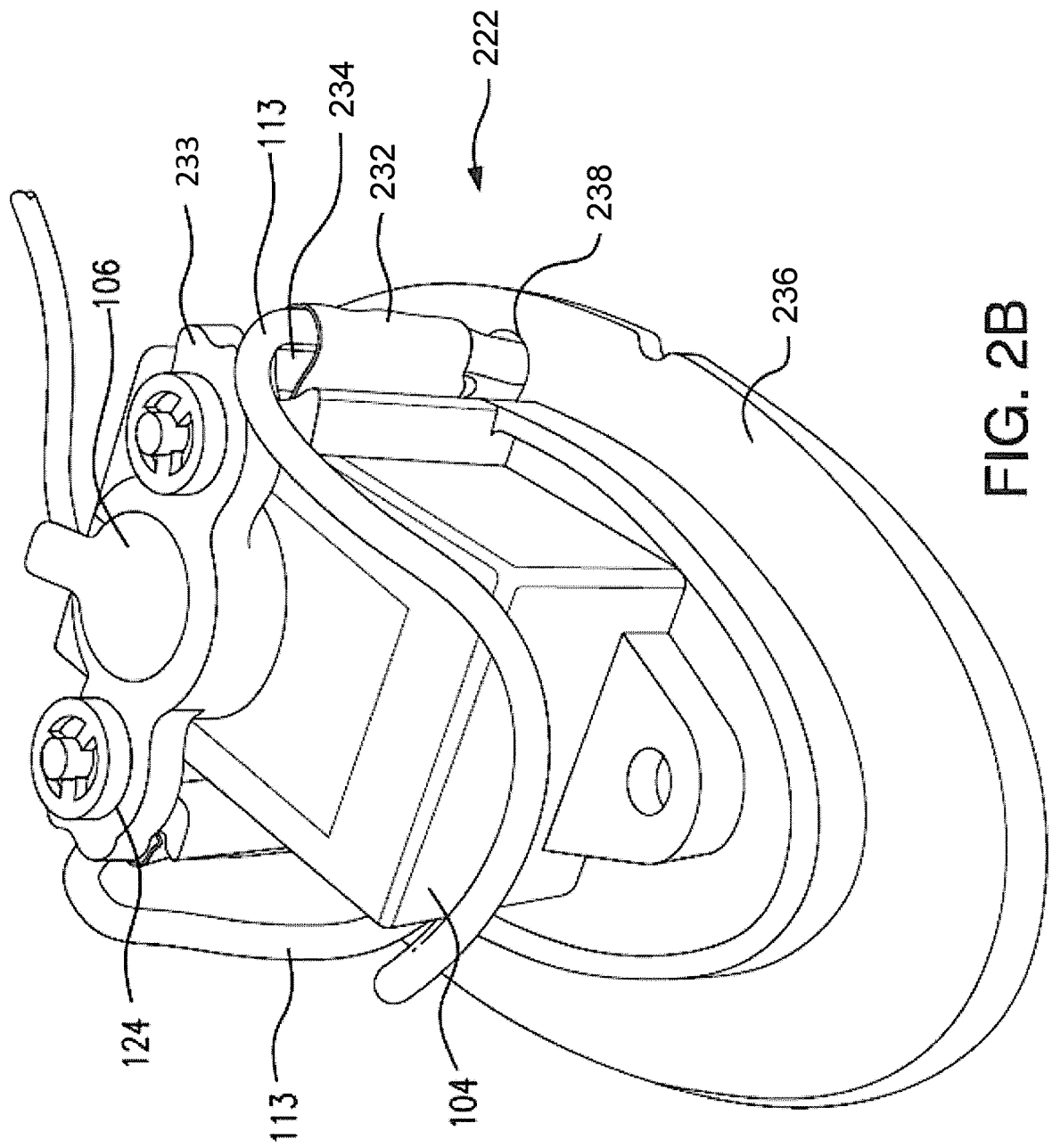

In some embodiments, the mechanical coupling may include a base 122 or frame 222 in which the transducer 106 may be supported (also see FIGS. 2A and 2B). In some embodiments, the mechanical coupling may include one or more arms 114, each of which may transmit mechanical oscillatory energy from the transducer 106 to one or more of the respective electrodes 112a-112d. In some embodiments, one, some, or all of the arms 114 may be coupled to the base 122 or frame 222. Exemplary embodiments of the mechanical coupling are discussed in greater detail below with respect to FIGS. 2A and 2B.

In some embodiments, a single transducer 106 may be used. In some embodiments, the transducer 106 may be arranged to be substantially equidistant between a first electrode 112a on a first side of the housing 120 and a second electrode 112c on a second side of the housing. In some embodiments, the transducer 106 may be substantially equidistant from each of the electrodes 112a-112d. In this manner, oscillatory energy generated by the transducer 106 may be applied substantially equally to each of the electrodes 112a-112d.

In some embodiments, one, some, or all of the electrodes 112a-112d may be brushes having one or more bristles. In some embodiments, the bristles may be made from conductive materials such as metal or carbon. In some embodiments, application of energy by the transducers 106, 116a, 116b to the electrodes 112a-112d may cause one or more of the bristles to oscillate. In some embodiments, application of energy by the transducer 106 to the electrodes 112a-112d may cause one or more of the bristles to oscillate. In some embodiments, application of energy by the transducer 106 to the electrodes 112a-112d may cause one or more of the bristles to oscillate at a magnitude that is greater than the oscillations produce by application of energy to the electrodes 112a-112d by the transducers 116a, 116b. In some embodiments, the transducers 116a, 116b may be ultrasound transducers that induce micro oscillations in the bristles of the electrodes 112a-112d, and the transducer 106 may be a vibration motor that induces higher magnitude mechanical oscillations in the bristles of the electrodes 112a-112d.

In some embodiments, one or more of the electrodes 112a-112d may be negative ionizing electrodes. In some embodiments, one or more of the electrodes 112a-112d may be positive ionizing electrodes. In some embodiments, the system may include both negative and positive ionizing electrodes (e.g., a bi-polar system). In some embodiments, one or more of the electrodes may oscillate between positive and negative polarity. Using both negative and positive ionizing electrodes may beneficially reduce the likelihood of surfaces (such as the interior housing walls) becoming charged and attracting particulate build-up.

In some embodiments, positive ionizing electrodes may be separated from negative ionizing electrodes by a distance. In some embodiments, a positive ionizing electrode 112a may be separated from a negative ionizing electrode 112c by a distance that is at least one third of the length L of the housing 120. In some embodiments, the distance may be at least one half of the length L of the housing. In some embodiments, the distance may be at least three fourths of the length L of the housing. Separating positive and negative electrodes in this manner may reduce the rate at which positive and negative ions collide and neutralize one-another, thereby improve the purification efficiency of the system. In some embodiments, structural elements may be positioned between a positive electrode 112a and a negative electrode 112c. For example, one or more of the ionizer 104, base 122 (or frame 222), and control board 102 may be placed between the positive electrode 112a and the negative electrode 112c. Disposing such elements between the positive and negative electrodes may also reduce the rate at which positive and negative ions collide and neutralize one-another.

In some embodiments, the controller 102 may be a circuit board, processor, or any other suitable device for controlling operation of electronic components. In some embodiments, the controller 102 may be configured to control other components of the system, such as the transducers, ion generator, and/or electrodes. For example, the controller may be configured to control transducers 116a, 116b and the transducer 106 such that at a first time, one or more of the transducers 116a, 116b apply energy to one or more respective electrodes 112a-112d and transducer 106 does not apply energy to one, some, or all of the electrodes 112a-112d. In some embodiments, the controller may be configured such that at a second time, transducer 106 applies energy to one, some, or all of the electrode 112a-112d.

In some embodiments, the controller may have a powered-on state and a powered off-state. In some embodiments, the controller may be configured such that when the controller is in a powered-on state, one or more of transducers 116a, 116b apply energy to one or more of the electrodes 112a-112d continuously or substantially continuously. In some embodiments, transducer 106 may be operably connected to a timing circuit such that the transducer 106 applies energy at intervals. In some embodiments, the intervals may be regularly spaced and/or may occur at predetermined times. In some embodiments, the timing circuit may be incorporated in the controller 102.

Figure 1B:
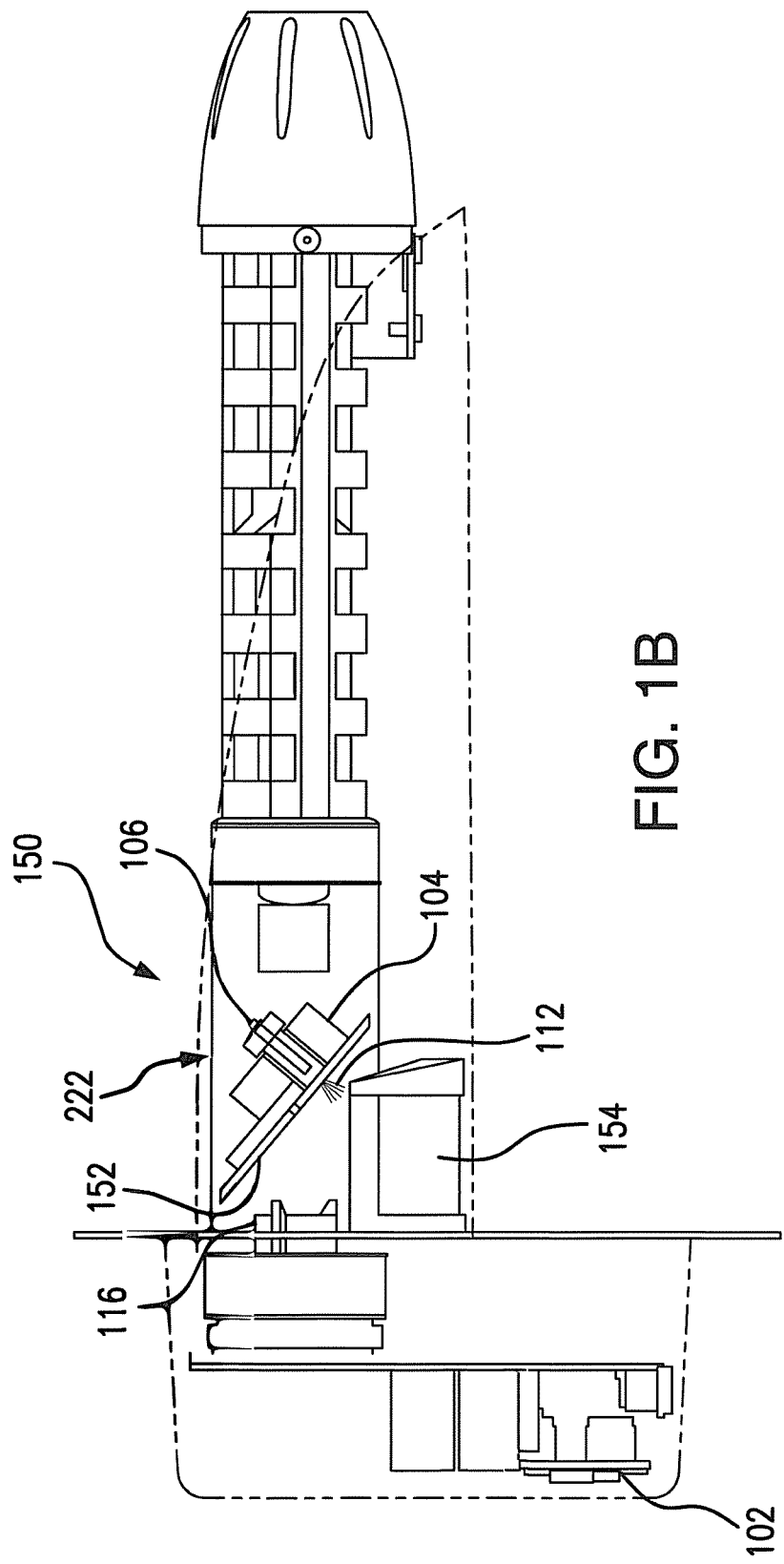

FIG. 1B illustrates another exemplary embodiment of a system 150 for purifying an environment. The system 150 may generally include the structural elements described with respect to FIG. 1A. In some embodiments, the system may include a controller 102, an ion generator 104, a first transducer 106, a second transducer 116, an electrode 112, and a frame 222. The details of the frame 222 are described in greater detail below with respect to FIG. 2B. Additionally, the system 150 may include a reflector 152 which may be angle to reflect ultrasonic energy produced by the transducer 116 toward a wick structure 154. Applying ultrasonic energy to the wick structure 154 may generate advanced oxidation products as described in U.S. patent application Ser. No. 14/542,484, which is incorporated by reference herein in its entirety.

FIG. 2A illustrates an exemplary embodiment of a base 122. In some embodiments, the base 122 may be a single integrally formed piece. For example, the base 122 may be an injection molded piece. In other embodiments, component parts of the base may be manufactured separately and then assembled.

In some embodiments, the base may include a receptacle 126 for receiving a transducer 106. In some embodiments, the receptacle 126 may be located substantially centrally on the base 122. In some embodiments, the base may be integrally formed with one or more arms 114. In other embodiments, the base 122 may be coupled to the housing 120 by any suitable coupling such as screws, bolts, friction coupling, or other arrangements. In some embodiments, the arms 114 may be elongated. In this manner, the magnitude of oscillations resulting at the tip ends of the arms may be increased. For example, in some embodiments, the length of one, some, or each of the arms 114 may be greater than one eighth of the length L of the housing. In other embodiments, the length of one, some, or each of the arms 114 may be greater than one fourth or one third of the length L of the housing.

In some embodiments, one, some, or all of the electrodes may be mechanically coupled to respective arms 114 such that vibration on a given arm will be transferred to an associated electrode. For example, in some embodiments, one, some, or all of the electrodes 112 may be coupled to the ion generator 104 via respective cables 113. In some embodiments, a distal portion of the cable near a given electrode may extend through a channel 128 formed in an associated arm 114. In some embodiments, the channel may be U-shaped with an opening along one side thereof in order to facilitate placement of the cable 113 within the channel 128. In other embodiments, the channel may fully enclose the cable 113. In still other embodiments, other suitable arrangements may be used to mechanically couple the electrodes 112 to the arms 114. This coupling could be accomplished, for example, via screws, bolts, friction coupling, or welding.

In some embodiments, one, some, or each of the arms 114 may be designed to maximize transmission of oscillatory energy from the transducer 106 to a respective electrode 112. For example, an arm 114 may have a cross-sectional shape that is substantially thicker along a major axis than along a minor axis. For example, an arm 114 may have a rectangular or oval cross-section. The arm may therefore be flexible and receptive to vibration in the minor axis plane but may resist vibration in the major axis plane. In this manner, vibration may be substantially confined to and/or maximized within a single plane. In some embodiments, the transducer 106 may be arranged relative to the base 122 such that the transducers generates oscillatory energy that is maximized in the plane in which the arms 114 are receptive to vibration (e.g., a minor axis plane of one or more of the arms 114).

In some embodiments, the arms 114 may include a joint portion 130 which may be directly coupled to the receptacle 126 in which the transducer 106 may be disposed. In some embodiments, the joint portion 130 may have a cross-sectional shape that is substantially thicker along a major axis than along a minor axis as described above. In some embodiments, the joint portion 130 may have no angular reinforcements such that the flexibility of the joint portion to oscillate is maximized. In some embodiments, two or more arms 114 may branch off of a given joint portion 130.

In some embodiments, the base 122 may be coupled to the housing 120 via one or more connectors 124. In some embodiments, the connectors 124 may be made from materials that dampen or absorb mechanical oscillation. For example, the connectors 124 may be silicone isolation dampeners. In other embodiments, the connectors may be rubber, metal or plastic springs, oil dampers, or any other suitable connector. Dampening materials may advantageously be used to reduce energy transmission to the housing 120, which can reduce movement of the frame and noise emitted by the system, as well as to help increase the oscillatory effect of the transducer 106 to the electrodes 112.

FIG. 2B depicts another exemplary embodiment of a mechanical coupling embodied here as a frame 222. The function of the frame 222 may be analogous to that of the base 122 described above, and the particular arrangements of elements, including the electrodes and transducers, described above may be equivalently incorporated into this embodiment of the mechanical coupling. In some embodiments, the frame 222 may be installed in an air purification system 150 as described with respect to FIG. 1B. In some embodiments, the frame 222 may include a top portion 233 which may be coupled to a support 236. In some embodiments, a first transducer 106 may be placed in a receptacle in the top portion 233. In some embodiments, an ion generator 104 may be disposed between the top portion 233 and the support 236. In some embodiments, an outer surface of the support 236 may define a reflector 152 as illustrated in FIG. 1B. In some embodiments, the frame 222 may be coupled to a housing of the system via connectors 124, which may, for example, be disposed adjacent a surface of the top portion 233.

In some embodiments, cables 113 may extend between the ion generator 104 and one or more electrodes 112. In some embodiments, the cables 113 may extend through one or more apertures 238 in the support 236 such that the electrodes may extend from an outer surface of the support (see also FIG. 1A). In some embodiments, the cables 113 may also extend through a channel in a coupling 232. In some embodiments, the coupling 232 may perform a similar function to the arms 114 discussed with respect to FIG. 2A. For example, the coupling 232 may transmit mechanical energy generated by the transducer 106 to the cables 113 and thereby to the electrodes 112. In some embodiments, a coupling 232 may be a tube (e.g., a shrink tube) that wraps around a cable 113 and a leg 234 of the top portion 233.

Figure 3:
FIG. 3 depicts an electrode that is formed as a brush for a purification system according to some embodiments.

FIG. 3 depicts an exemplary embodiment of an electrode 112 that is formed as a brush that includes a plurality of bristles. In some embodiments, the geometry, dimensions, and material properties of one or more of the electrodes 112a-112d may be selected to oscillate in such a manner as to maximize oscillations of the electrodes 112a-112d, which in turn may maximize the elimination of particulate build-up on the electrodes 112a-112d when the transducer 106 applies an oscillatory energy thereto. For example, in embodiments where the electrodes are formed as brushes, the bristles may have a length that is greater than a transverse dimension of the brush. In some embodiments where a brush electrode is used, the transverse dimension may be a diameter of the bundled plurality of bristles. In some embodiments, the length of the bristles may be approximately two, four, six, eight, ten, twelve, or more times the transverse dimension. It has been determined that a bristle length of approximately eight times the transverse dimension is particularly effective for removing particulate build-up when oscillatory energy is applied.

Figure 4:
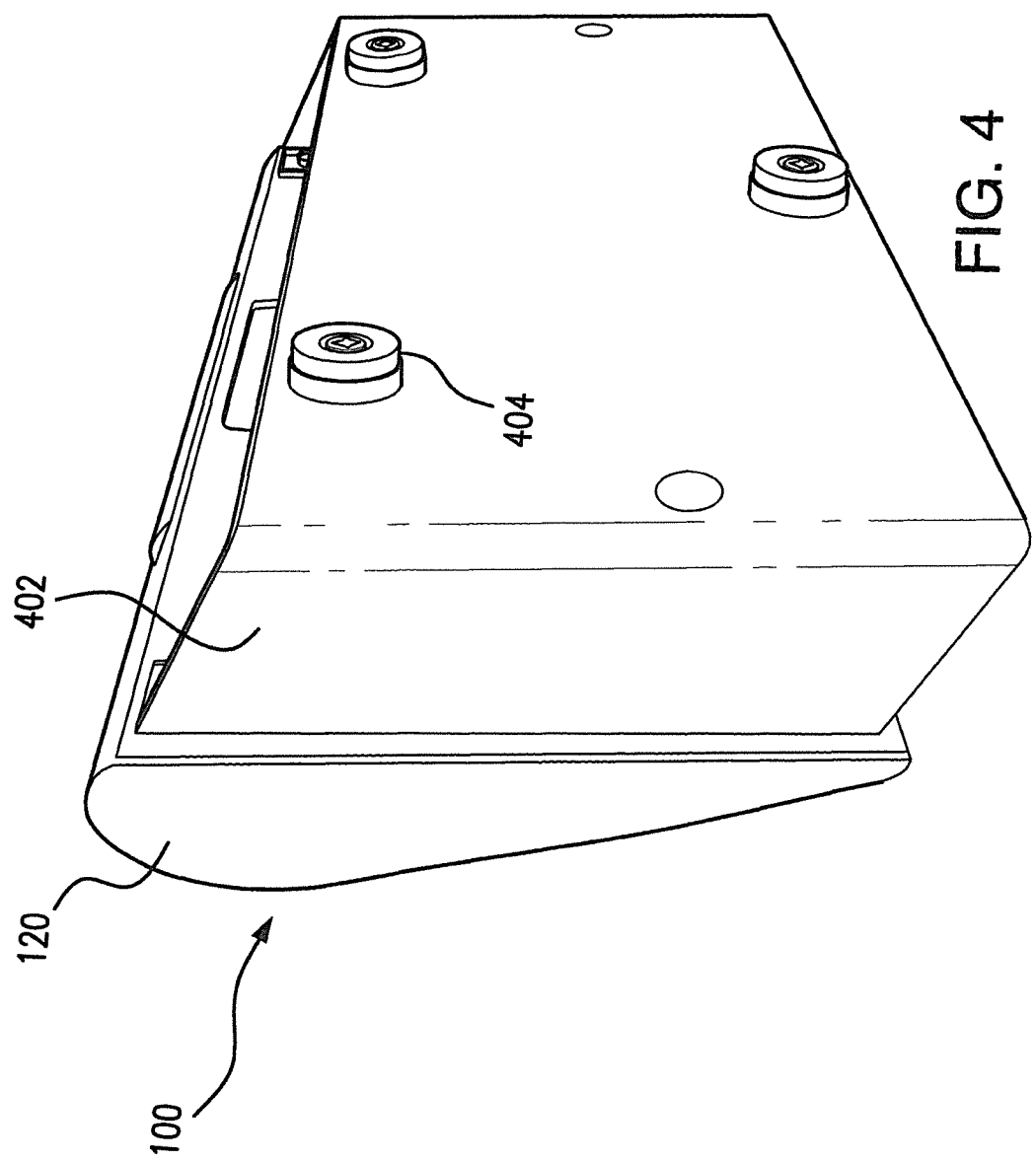
FIG. 4 depicts a mounting for a purification system according to some embodiments.

FIG. 4 depicts an exemplary embodiment in which the housing 120 is affixed to a mounting bracket 402. In some embodiments, the mounting bracket 402 may include one or more magnetic feet 404, which may be used to mount the system 100 to ferrous surfaces such as a wall of an HVAC system or component thereof (see FIGS. 5 and 6). Other suitable arrangements may be used for mounting the system in any desired location to purify an environment. For example, double-sided tape, screws, and hook-and-loop coupling mechanisms can be used for mounting the system. Hook-and-loop adhesive tape can be particularly advantageous when mounting the system to an HVAC system such as a mini-split (for example, see FIG. 7).

Figure 5:
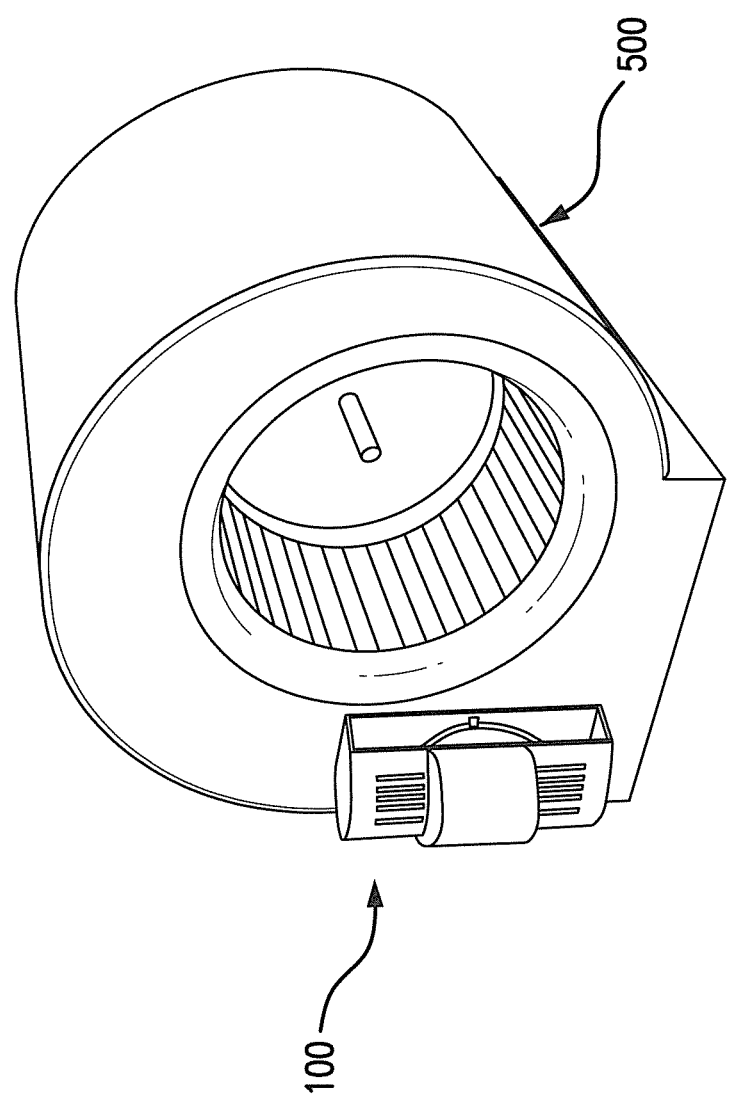

FIG. 5 depicts an exemplary embodiment where a purification system 100 is mounted to a component 500 of an HVAC system. The component 500 can be, for example, an air handler unit or a blower unit. In some embodiments, the system 100 can be arranged near an intake of an HVAC component such that a portion of the air flowing into the component 500 will pass through the system housing, thereby mixing ions generated by the system 100 into the airflow of the HVAC component. By mixing ions into this airflow, a degree of purification may be advantageously applied to the entire airflow passing through the HVAC component 500.

Figure 6:
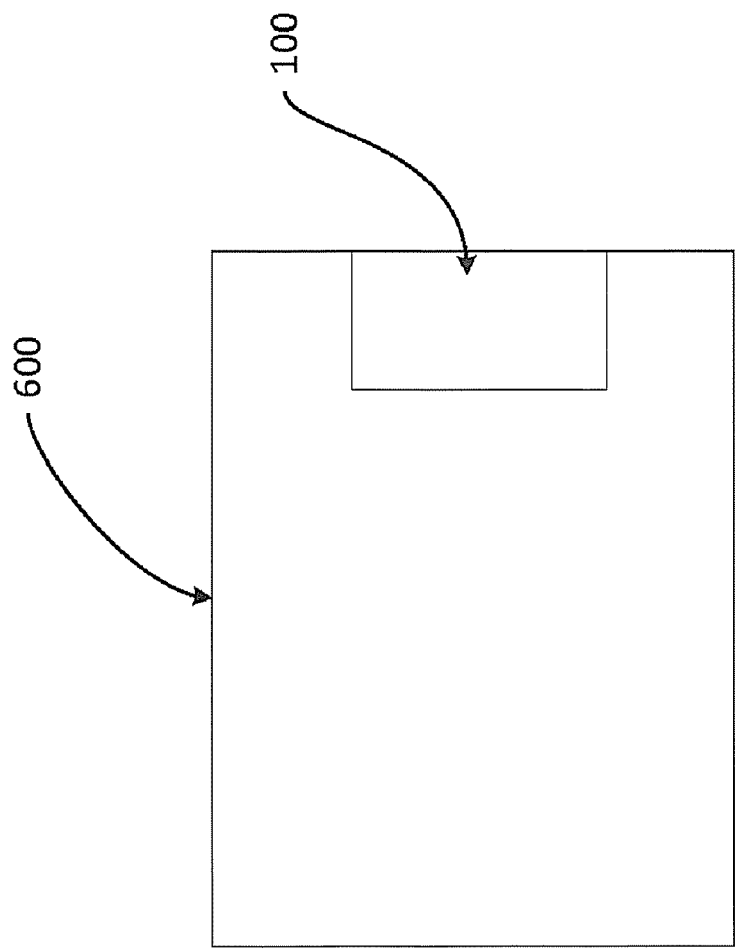

FIG. 6 depicts an exemplary embodiment wherein a purification system 100 is mounted to a wall within a duct 600 of an HVAC system. As discussed above with respect to FIG. 5, ions generated by the system 100 may pass into the airflow through the duct 600, thereby purifying the passing air.

FIG. 7 depicts an exemplary embodiment wherein a purification system 100 is mounted to a mini-split HVAC system 700. The purification system may be mounted proximate an air intake of the HVAC system 700 such that ions generated by the system will mix into the airflow through the HVAC system 700. As discussed above with respect to FIGS. 5 and 6, this may advantageously apply a purification effect to the entire airflow passing through the HVAC system 700.

FIG. 8 depicts an exemplary method 800 for purifying an environment. The method may be performed, for example, in a system including a housing, a first electrode, a first transducer configured to apply a first energy, a second transducer configured to apply a second energy, and a controller. In step 802 an air flow may be received into the housing. The air flow may include a plurality of air molecules. The flow may be received, for example, within the housing. In step 804, at least one of the air molecules may be ionized using the first electrode. In step 806, the first transducer may apply a first energy to the first electrode while the second transducer does not apply the second energy to the first electrode. In step 808, the second transducer may apply the second energy to the first electrode.

In some embodiments, the steps of applying the first energy and/or the second energy to the first electrode may be effective to remove particulate build-up from the first electrode. In some embodiments, the first electrode may be a brush comprising a plurality of bristles, and applying the first energy to the first electrode may cause one or more bristles of the plurality of bristles to oscillate. In some embodiments, applying the second energy to the first electrode may cause the one or more bristles of the plurality of bristles to oscillate at a greater magnitude than does applying the first energy to the plurality of bristles. In some embodiments, method 800 may further comprise determining, using a timing circuit, that an interval of time has elapsed since the second energy was last applied to the first electrode, and in response to determining that the interval of time has elapsed, applying the second energy to the first electrode. This optional determining step may be performed, for example, by the controller.

Disclosed herein are systems and methods for purifying an environment. These systems and methods confer numerous advantages. For example, use of two different types of energy (e.g., ultrasonic energy and mechanical oscillations) targets particles of different sizes and provides redundancy to maximize the elimination of particulate build-up, even if one of the transducers fails. By continuously targeting ultrasonic energy onto the electrodes, it is possible to induce micro oscillations, which help in greatly reducing the accumulation of this build up, especially of the very small particulates. At the same time, this ultrasonic technology may also act as pest deterrent to species that are caused discomfort by this energy level. Further, application of ultrasonic energy requires little power, which promotes high efficiency and low cost for use. By using a second type of transducer, such as a vibration motor, particles too large to be effectively removed by the first type of transducer may still be removed. Another advantage of the present disclosure is that the electrodes may be continuously cleaned without the need to directly contact the electrodes with any external mechanical force. The electrodes therefore never need to be contacted by an external object, which saves time and effort in maintaining the system and extends the useful life of the system.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

The invention claimed is:

1. A system for purifying an environment, the system comprising:
    a first electrode, the first electrode being exposed to air;
    a first transducer, the first transducer being configured to apply a first energy to the first electrode;
    a second transducer, the second transducer being configured to apply a second energy to the first electrode, wherein the second energy is a different type of energy than the first energy;
    a controller, the controller being configured to control the first transducer and/or the second transducer, wherein the system is configured such that:
    at a first time, the first transducer applies the first energy to the first electrode and the second transducer does not apply the second energy to the first electrode; and
    at a second time, the second transducer applies the second energy to the first electrode.

2. The system of claim 1, wherein the first electrode is a brush comprising a plurality of bristles.

3. The system of claim 2, wherein applying the first energy to the first electrode causes one or more bristles of the plurality of bristles to oscillate.

4. The system of claim 3, wherein applying the second energy to the first electrode causes the one or more bristles of the plurality of bristles to oscillate at a greater magnitude than does applying the first energy to the plurality of bristles.

5. The system of claim 2, wherein the brush has a length and a transverse dimension perpendicular to its length, the length being at least 4 times the transverse dimension.

6. The system of claim 1, wherein the first transducer is an ultrasonic transducer and the second transducer is a vibration motor that emits mechanical oscillatory energy.

7. The system of claim 1, wherein the first energy is applied to the first electrode substantially continuously when the controller is in a powered-on state.

8. The system of claim 1, wherein the second transducer is operably connected to a timing circuit such that the second energy is applied to the first electrode at intervals.

9. The system of claim 1, further comprising a second electrode and a third transducer, the third transducer being configured to apply a third energy to the second electrode, wherein the second transducer is configured to apply the second energy to both the first electrode and the second electrode.

10. The system of claim 9, further comprising a housing which encloses the first electrode, the second electrode, the first transducer, the second transducer, and the third transducer, the housing having a length,
    wherein the first electrode has negative polarity and the second electrode has a positive polarity, the first electrode being separated from the second electrode by a distance, the distance being at least one third of the length of the housing.

11. A system for purifying an environment, the system comprising:
    a first electrode, the first electrode being exposed to air;
    a first transducer, the first transducer being configured to apply a first energy to the first electrode;
    a controller, the controller being configured to control the first transducer, wherein the system is configured such that:
    at a first time, the first transducer applies the first energy to the first electrode; and
    at a second time, the first transducer does not apply the first energy to the first electrode;
    a second transducer, the second transducer being configured to apply a second energy to the first electrode,
    wherein the second transducer includes an ultrasonic transducer and applying the second energy to the first electrode causes one or more bristles of the plurality of bristles to oscillate at a lesser magnitude than does applying the first energy to the plurality of bristles,
    wherein the second energy is applied to the first electrode substantially continuously when the controller is in a powered-on state.

12. The system of claim 11, wherein applying the first energy to the first electrode causes one or more bristles of the plurality of bristles to oscillate.

13. The system of claim 11, wherein the brush has a length and a transverse dimension perpendicular to its length, the length being at least 4 times the transverse dimension.

14. The system of claim 11, wherein the first transducer is a vibration motor.

15. The system of claim 11, wherein the first transducer is operably connected to a timing circuit such that the second energy is applied to the first electrode at intervals.

16. The system of claim 11, further comprising a second electrode, the first transducer being configured to apply the first energy to both the first electrode and the second electrode.

17. The system of claim 16, further comprising a housing which encloses the first electrode, the second electrode, and the first transducer, the housing having a length;
    wherein the first electrode has a negative polarity and the second electrode has a positive polarity, the first electrode being separated from the second electrode by a distance, the distance being at least one third of the length of the housing.

18. The system of claim 16, further comprising a mechanical coupling configured to conduct vibration energy, the mechanical coupling being coupled to each of the first transducer, the first electrode, and the second electrode;
    wherein the first transducer is substantially equidistant between the first electrode and the second electrode.

* * * * *